(12) United States Patent
Lee et al.

(10) Patent No.: US 6,207,379 B1
(45) Date of Patent: Mar. 27, 2001

(54) METHOD FOR AMPLIFICATION OF DNA

(75) Inventors: Jar-How Lee; Lindley Blair, both of Los Angeles, CA (US)

(73) Assignee: One Lambda, Canoga Park, CA (US)

(*) Notice: Subject to any disclaimer, the term of this patent is extended or adjusted under 35 U.S.C. 154(b) by 0 days.

(21) Appl. No.: 09/151,465

(22) Filed: Sep. 11, 1998

(51) Int. Cl.[7] ............................... C12Q 1/68; C12P 19/34
(52) U.S. Cl. ........................ 435/6; 435/91.2; 435/91.1
(58) Field of Search ..................... 435/6, 91.2, 91.1; 536/23.1, 24.3

(56) References Cited

U.S. PATENT DOCUMENTS

| 4,683,195 | 7/1987 | Mullis et al. | 435/6 |
|---|---|---|---|
| 4,683,202 | 7/1987 | Mullis | 435/91 |
| 5,595,890 | 1/1997 | Newton et al. | 435/91.2 |
| 5,785,835 | 7/1998 | Saito et al. | 204/616 |

FOREIGN PATENT DOCUMENTS

| 0 237 362 A1 | 9/1987 | (EP) . |
|---|---|---|
| 0 258 017 A2 | 3/1988 | (EP) . |
| 0 332 435 B1 | 9/1989 | (EP) . |
| WO 87/06270 | 10/1987 | (WO) . |
| WO 88/10315 | 12/1988 | (WO) . |

OTHER PUBLICATIONS

Bodmer et al., *Tissue Antigens*, 49:297–321 (1997).
Bunce et al., *Tissue Antigens*, 43:7–17 (1994).
Bunce et al., *Tissue Antigens*, 46:335–367 (1995).
DuPont, *Tissue Antigens*, 46:353–354 (1995).
Horton et al., *BioTechniques*, vol. 8, No. 5, 528 (1990).
Lizardi et al., *Biotechnology*, vol. 6, 1197–1202 (Oct. 1988).
Olerup et al., *Tissue Antigens*, 41:119–134 (1993).
Senanayake et al., *Molecular Biology*, vol. 4, 13–15 (1995).
Zoller et al., *Methods in Enzymology*, vol. 154, 329–350 (1987).

*Primary Examiner*—W. Gary Jones
*Assistant Examiner*—Jehanne Souaya
(74) *Attorney, Agent, or Firm*—Marshall, O'Toole, Gerstein, Murray & Borun

(57) ABSTRACT

The invention provides methods for detecting target nucleic acid sequences with diagnostic primers including priming regions and probe regions which are complementary to target and reference regions respectively on a sample nucleic acid strand wherein the probe region is located 5' to the priming region which is complementary to a reference nucleic acid sequence which is 3' to the target nucleic acid sequence on the sample nucleic acid strand wherein when said reference nucleic acid sequence is contiguous with said target nucleic acid sequence on the sample nucleic acid strand then the priming region and probe region on the diagnostic probe are separated by a spacer region of nucleic acid.

8 Claims, 2 Drawing Sheets

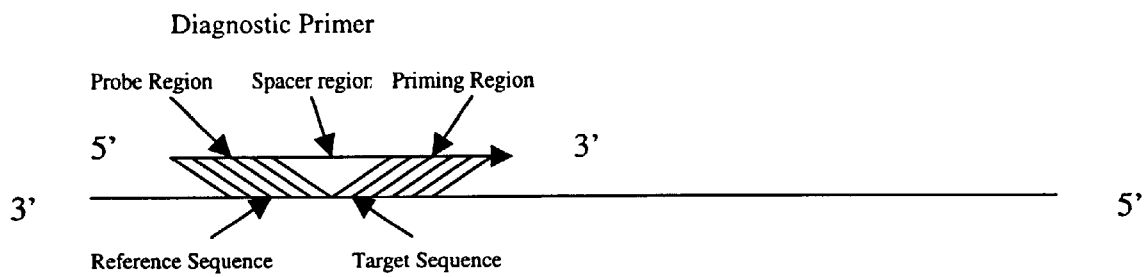
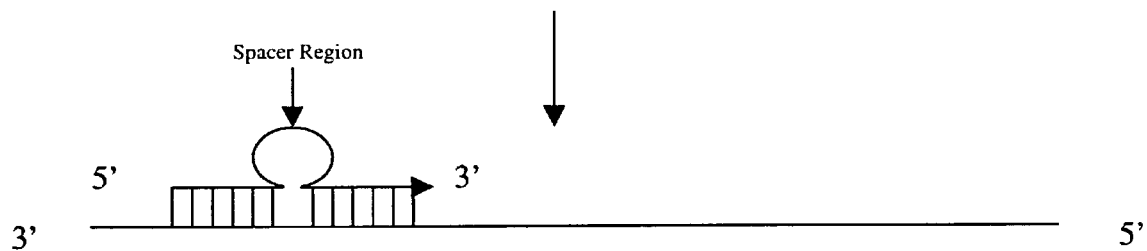
FIG. 2A
FIG. 2B
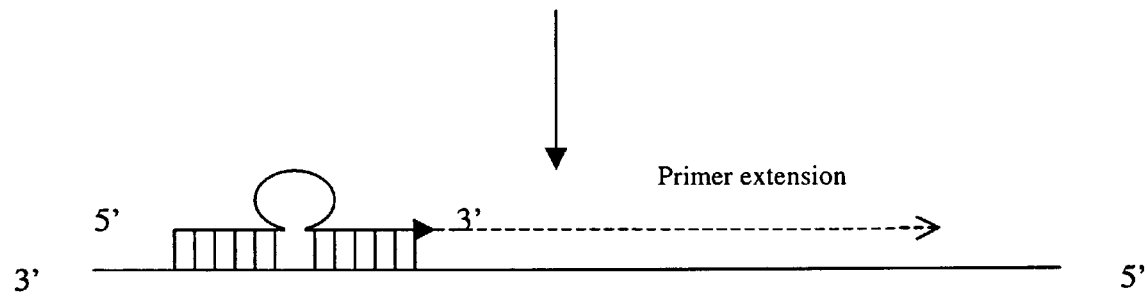
FIG. 2C

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: primer
      OLR-14

<400> SEQUENCE: 1
cttggagtac tctacgtct                                               19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: primer
      OLR-142

<400> SEQUENCE: 2
gcagtagttg tccacccg                                                18

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer
      OLR-1414

<400> SEQUENCE: 3
ttggagtact ctacgtctga aggttcctgg ag                                32
```

```
<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: primer
      OLR-1419

<400> SEQUENCE: 4
ttggagtact ctacgtctga ttcctggaga ga                                 32

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: primer
      OLR-1420

<400> SEQUENCE: 5
ttggagtact ctacgtctga tcctggagag ata                                33

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: primer
      OLR-1334

<400> SEQUENCE: 6
gaccggaaca cacggttggc ccagt                                         25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: primer
      OLR-1348

<400> SEQUENCE: 7
actcaccgtc ctcgcaatag tagcc                                         25
```

METHOD FOR AMPLIFICATION OF DNA

BACKGROUND OF THE INVENTION

The present invention relates to methods for the detection of the presence or absence of nucleic acid sequences which are characteristic of pathogens and the like as well as of gene variations and mutations including those relating to the human leukocyte antigen (HLA) which is of interest in the field of human transplantation.

The HLA locus is highly polymorphic in nature. As disclosed in the Nomenclature for Factors of the HLA System 1996 (Tissue Antigens 1997: 49:297–321), there are 83 HLA-A alleles, 186 HLA-B alleles, 42 HLA-C alleles, 184 HLA-DRB1 alleles, 11 DRB3 alleles, 8 DRB4 alleles, 12 DRB5 alleles, 18 DQA1 alleles and 31 DQB1 alleles, with new alleles being discovered continuously. All HLA-A, -B, and -C alleles have similar sequences. The same holds for DRB1, DRB3, DRB4 and DRB5 sequences. Because of these similarities, very often when a primer pair is used in the practice of polymerase chain reaction sequence-specific priming (PCR-SSP), two or more alleles will be amplified. Therefore, for each allele to have a unique PCR-SSP pattern many pairs of primers must be used. Accordingly, in clinical use of PCR-SSP for HLA typing there exists a desire to use a limited number of PCR reactions to achieve as much resolution as possible whereby the number of alleles amplified by a pair of primers would be reduced (i.e., the specificity of the primers increased). Simultaneously, all of the primer pairs must have optimal annealing temperatures within a very restricted range.

PCR requires a pair of primers flanking the region on the DNA template for that region to be amplified. The ability of a primer to anneal to the desired sequence depends on the length of the primer and the annealing temperature set in the PCR thermocycling program. The longer the primer, the higher the annealing temperature it needs to achieve specific amplification of a DNA sequence. If the annealing temperature for a PCR is above the optimal range for the primer to anneal to its target, little or no amplification will occur. If the annealing temperature for a PCR is below the optimal range for the primer to anneal to its target, non-specific amplification will occur. PCR-SSP uses a balance between primer length and annealing temperature to achieve the specificity of the primer-directed sequence amplification. This technique can be used to characterize the sequence on the target DNA template—if amplification occurs, the template DNA contains the same sequences as the primers used; if no amplification occurs, the sequences on the template DNA are different from the primer sequences. Of interest to the present application are the disclosures of Olerup et al., Tissue Antigens 41: 119–134 (1993) and Bunce et al., Tissue Antigens 43: 7–17 (1994) which teach methods of PCR-SSP for HLA typing.

Newton et al., U.S. Pat. No. 5,595,890 disclose PCR diagnostic methods for typing including molecular typing of HLA using PCR-SSP. According to this method, an unknown allele is assigned based on the pattern of positive or negative reactions from multiple PCR. The methods disclosed by Newton are limited in their effectiveness for HLA typing, however, due to the high degree of polymorphism in HLA as described above. As a consequence two primers, each with specific sequences, frequently amplify many HLA alleles, thus increasing the required number of PCR in order to assign an unknown allele.

Accordingly, there exists a desire in the art for improved methods of PCR-SSP based molecular typing whereby the specificity of the typing can be increased so as to reduce the number of PCR reactions required for each typing.

SUMMARY OF THE INVENTION

The present invention relates to improved methods for detecting and/or amplifying target nucleic acid sequences and in particular for the detection and amplification of human leukocyte antigens (HLA) through methods such as polymerase chain reaction whereby the specificity of diagnostic primers is increased such that at least one primer is capable of recognizing two or more regions on the template and is preferably capable of doing so without increasing the annealing temperature of the primer to the template DNA. The increased specificity of the primer set reduces the number of alleles amplified by that primer pair and provides improved resolution over conventional PCR-SSP at lower cost.

Specifically, the invention provides a method for detecting the presence of a target nucleic acid sequence on a sample nucleic acid strand from an individual comprising the steps of: treating the sample, together or sequentially with appropriate nucleoside triphosphates, an agent for polymerization of the nucleoside triphosphates, a diagnostic primer and an amplification primer under hybridizing conditions; wherein the nucleotide sequence of said diagnostic primer comprises (1) a priming region at its 3'-end which is substantially complementary to the target nucleic acid sequence, and (2) a probe region located 5' to said priming region which is substantially complementary to a reference nucleic acid sequence which is 3' to the target nucleic acid sequence on the sample nucleic acid strand wherein when said reference nucleic acid sequence is contiguous with said target nucleic acid sequence on the sample nucleic acid strand then the priming region and probe region on the diagnostic probe are separated by a spacer region of nucleic acid, whereby for selected hybridization and extension conditions an extension product of the diagnostic primer is synthesized when the priming region is substantially complementary to the target nucleic acid sequence and when the probe region is substantially complementary to the reference nucleic acid sequence, but wherein for said selected hybridization and extension conditions no extension product of the diagnostic primer is synthesized when either the priming region or the probe region are not substantially complementary to the target and reference nucleic acid sequences respectively; any extension product of the diagnostic primer formed being capable of serving as a template for synthesis of an extension product of said amplification primer after separation from its complement; amplifying any extension product; and detecting the presence or absence of the target polynucleic acid sequence from the presence or absence of amplification product obtained as above. According to a preferred aspect of the present invention, the priming region and probe regions are exactly complementary to the target and reference nucleic acid sequences respectively.

While the priming region and the probe region can be contiguous on the diagnostic primers of the invention they need not be. Thus, according to one preferred embodiment of the invention the priming region and the probe region may be separated by a spacer region of nucleic acid sequence which is not complementary to the sequence of the sample nucleic acid strand between the target and reference sequence. Specifically, the spacer region is selected so as to provide a discontinuity in the complementarity of the nucleotide sequences of the priming and probe regions of the diagnostic primer such that hybridization and extension of the primer region will not occur unless the probe region is substantially complementary to the reference nucleic acid sequence.

The spacer region can be from 1 to 30 nucleotides or more in length with lengths of from 8 to 30 nucleotides being preferred although those of skill in the art will recognize that in general the longer the spacer region the longer the priming region must be in order to successfully hybridize to the target nucleic acid sequence under the hybridization conditions selected for practice of the invention. Nevertheless, the length of the spacer region, as well as the length of intervening sequence between the target nucleic acid sequence and the reference nucleic acid sequence on the sample nucleic acid strand which can be from 0 to 350 bases or more should not be so long that the priming region is able to hybridize independently to the target nucleic acid sequence by virtue of increased length (and therefore increased annealing temperature) without requiring prior hybridization of the probe region to the reference nucleic acid sequence.

The present invention additionally provides kits for practice of the methods of the invention which comprise a diagnostic primer according to the invention in combination with each of four nucleoside triphosphates and an agent for polymerization of the nucleoside triphosphates. The kits can also optionally comprise an amplification primer being such that any extension product of the corresponding diagnostic primer may, after separation from its complement, serve as a template for synthesis of an extension product of the amplification primer.

BRIEF DESCRIPTION OF THE DRAWINGS

FIGS. 2a, 2b and 2c depict a second embodiment of the present invention wherein the reference sequence is contiguous with the target sequence on the sample nucleic acid strand and the diagnostic primer comprises a spacer sequence disposed between the probe region and the priming region.

DETAILED DESCRIPTION

Figure 1A:
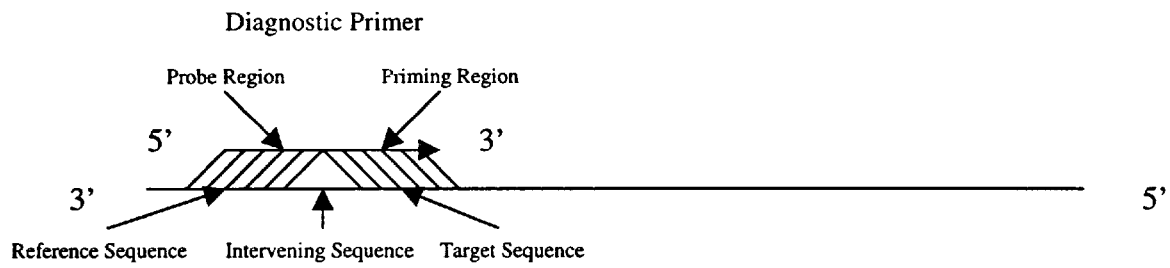
FIGS. 1a, 1b and 1c depict a first embodiment of the present invention wherein the reference sequence is 3' to the target sequence on the sample nucleic acid strand.

The present invention relates to nucleic acid primers which may be used in a variety of manners but which are particularly useful for use in PCR amplification of DNA. Rather than using a conventional design of primer, which both recognizes a DNA sequence by complementarity and acts as a primer for synthesis by a DNA polymerase, the present invention provides primers characterized by having two different functions which comprise two (or more) non-consecutive DNA sequences on the same primer. According to the invention, first portion of the primer sequence, the probe region, functions primarily to specifically bind to a reference nucleic acid sequence on the target nucleic acid which is 3' to and preferably non-contiguous with the target nucleic acid sequence without having the restriction of being exactly complementary at the 3'-end, (which is usually required for efficient priming for a DNA polymerase to produce an extension product). Coupled at the 3'-end of the probe region is the priming region, which recognizes the target sequence on the sample nucleic acid strand. The priming region is preferably separated downstream from the probe region but may be contiguous if provided the reference nucleic acid sequence and target nucleic acid sequence on the sample nucleic acid strand are not contiguous. The priming region can also increase specificity of the primer as a whole and must be sufficiently complementary to the target sequence so that it can function to promote extension of the target sequence under appropriate hybridization and extension conditions.

According to practice of the invention the probe region functions to roughly align the primer to the region of interest on the sample nucleic acid strand (which according to one embodiment of the invention is the HLA region). The priming region is thereby more favorably disposed kinetically (by virtue of a local concentration effect) such that it can thereafter more readily recognize another nearby sequence (usually within a few hundred base pairs). Increased specificity for a particular allele can be provided if a suitable specific DNA sequence is nearby.

The priming sequence may add specificity to binding of the diagnostic primer, but also functions as the site to prime DNA synthesis by the DNA polymerase (usually a heat stable polymerase such as Taq polymerase). By using spacings for the target sequences that are within a restricted range, e.g. 50–350 bp on the template DNA, amplification products for virtually any allele can be separated from larger or smaller standard bands even on gel systems designed for a restricted size range (such as that described in U.S. Pat. No. 5,785,835 and available commercially as the Micro-SSP gel box, One Lambda, Inc. Canoga Park, Calif.). Practice of the present invention also provides particular advantages because keeping the use of shorter amplification products avoids problems associated with weak amplification of larger products in fast PCR programs.

The diagnostic primers of the present invention are particularly useful for use in carrying out the PCR reaction which typically relies on the sequence specificity of two primers used in the amplification step. Use of the diagnostic primers of the invention allows the PCR reaction to utilize more than two regions of sequence-specificity in a targeted DNA because each primer can contain more than one sequence-specificity. According to practice of the invention the length of the probe region can be shorter than would otherwise be optimal under selected hybridization and extension conditions as long as the probe region will recognize the target sequence with moderate efficiency. After the probe region anneals to the target sequence, the priming region will then readily anneal to its downstream target sequence.

The length of priming region should be selected to be below the length that would otherwise be optimal under the selected hybridization and extension conditions otherwise it would anneal to the target sequence on its own (and allow an extension product to be formed). Annealing of the probe region to the reference nucleic acid sequence on a nucleic acid strand containing the target sequence will increase the local concentration of the priming sequence to its target sequence, thus achieving successful annealing of the priming region to its target under sub-optimal conditions. Therefore, the priming region and the probe region are designed such that under given selected hybridization and extension conditions, an extension product of the diagnostic primer is synthesized when the priming region is substantially complementary to the target nucleic acid sequence and when the probe region is substantially complementary to the reference nucleic acid sequence, but wherein no extension product of the diagnostic primer is synthesized under those same hybridization and extension conditions when either the priming region or the probe region are not substantially complementary to the target and reference nucleic acid sequences respectively. Nevertheless, it will be understood that the selectivity of the diagnostic primers of the invention is dependent upon the hybridization and extension conditions selected for practice. Thus, those of skill in the art will recognize that higher annealing temperatures will generally require longer primer and probe sequences while lower annealing temperatures will generally require shorter primer and probe sequences. Other factors such as reagent concentrations and the GC content of the target and reference regions of the sample nucleic acid strand will also affect the design of the diagnostic primers of the invention.

Figure 1B:
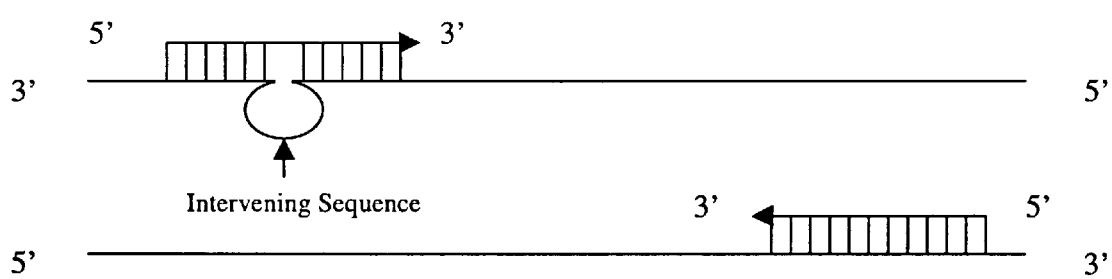
Figure 1C:
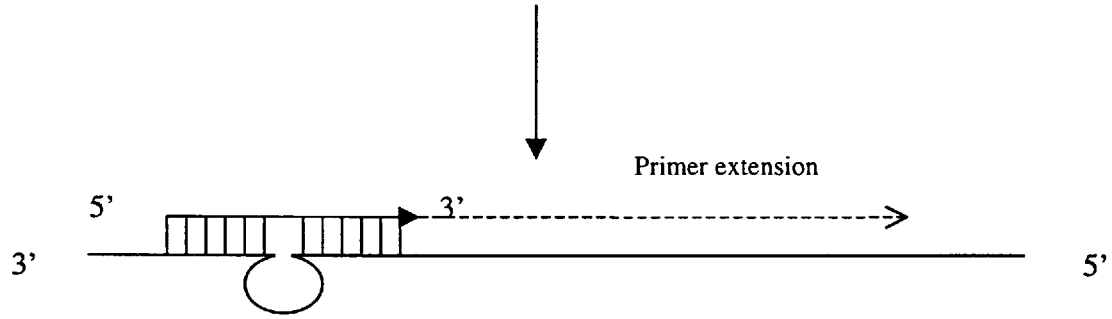
Figure 1C:

FIG. 1 depicts an embodiment of the present invention whereby a diagnostic primer comprising a probe region and a priming region which are not separated by a spacer region is used in combination with an amplification primer to detect the presence of a target nucleic acid sequence on a sample nucleic acid strand. Specifically, FIG. 1a depicts the hybridization of the probe region to a reference nucleic acid sequence which is 3' to the target nucleic acid sequence on the sample nucleic acid. Hybridization of the probe sequence to the reference sequence creates a local concentration effect such that under the selected hybridization and extension conditions the priming region of the diagnostic primer will hybridize to the target sequence on the sample nucleic. The hybridization and extension conditions are further selected given the identity of the target and the diagnostic primer that the priming region will not hybridize with the target sequence when the probe region is not hybridized to the associated reference sequence. FIG. 1a further depicts hybridization of an amplification primer to another sequence associated with the target nucleic acid sequence. FIG. 1b depicts hybridization of the probe region and priming region of the diagnostic primer to the reference sequence and target sequence on the sample nucleic acid respectively and the formation of a "hairpin" by the intervening sequence between the reference sequence and the target sequence on the sample nucleic strand which have hybridized to portions of the diagnostic primer. FIG. 1c depicts extension of the diagnostic and amplification primers under extension conditions in the presence of appropriate nucleoside triphosphates and a polymerase. The extension product of the diagnostic primer may then be used as a template for synthesis of an extension product of the amplification primer after separation from its complement and the extension product may be amplified and detected according to conventional methods.

FIG. 2 depicts a second embodiment of the present invention whereby a diagnostic primer comprising a probe region and a priming region separated by a spacer region is used in combination with an amplification primer to detect the presence of a target nucleic acid sequence on a sample nucleic acid strand. In this case, the target nucleic acid sequence is associated with a reference nucleic acid sequence which is contiguous with the target nucleic acid sequence on the sample nucleic acid strand. Specifically, FIG. 2a depicts the hybridization of the probe region to a reference nucleic acid sequence which is 3' to the target nucleic acid sequence on the sample nucleic acid. Hybridization of the probe sequence to the reference sequence creates a local concentration effect such that under the selected hybridization and extension conditions the priming region of the diagnostic primer will hybridize to the target sequence on the sample nucleic. The hybridization and extension conditions are further selected given the identity of the target and the diagnostic primer that the priming region will not hybridize with the target sequence when the probe region is not hybridized to the associated reference sequence. FIG. 2a further depicts hybridization of an amplification primer to another sequence associated with the target nucleic acid sequence. FIG. 2b depicts hybridization of the probe region and priming region of the diagnostic primer to the reference sequence and target sequence on the sample nucleic acid respectively and the formation of a "hairpin" by the spacer region between the probe region and the priming region which is not complementary to the sequence of the sample nucleic acid strand between the target and reference sequences. FIG. 2c depicts extension of the diagnostic and amplification primers under extension conditions in the presence of appropriate nucleoside triphosphates and a polymerase. The extension product of the diagnostic primer may then be used as a template for synthesis of an extension product of the amplification primer after separation from its complement and the extension product may be amplified and detected according to conventional methods.

The present invention provides improvements over prior art typing methods such as those of Newton et al., U.S. Pat. No. 5,595,890 where multiple PCR reactions may be required to assign an unknown allele. Use of the diagnostic primers of the invention will add extra selectivity to the sequence specific primer method because more than two unique sequences can be used as the selection criteria for the PCR. Thus, the number of separate PCR reactions required for assigning an unknown allele may be reduced which reduces the cost of PCR-SSP testing. Selection of appropriate primers according to the invention will allow resolution of ambiguities that occur in some heterozygous cases wherein the multi-PCR pattern derived from two different alleles is identical to another pair of alleles.

The use of primers according to the invention allows greater specificity in the recognition of a specific allele or set of alleles by using more than one region of sequence homology to the nucleic acid sequence of interest. Increasing the specific recognition of nucleic acid sequence homology refines the ability to carry out a variety of DNA-based tests. Included among these tests would be HLA tissue typing, detection of genetically inherited diseases, detection of infectious organisms in tissue, or detection of a variety of other markers or conditions based on the presence of a nucleic acid sequence (e.g. for testing the efficacy of a gene therapy technique). The diagnostic primers of the invention may also be used in methods for the transcriptional base amplification and Q-Replicase base amplification.

It will be further appreciated that any extension product obtained may if desired be amplified by the polymerase chain reaction (PCR) as described in U.S. Pat. Nos. 4,683,195 and 4,683,202, by the use of Q-beta replicase described in PCT Patent Publication WO 87/06270 and in Biotechnology Vol. 6, October 1988, by the use of the transcription based nucleic acid amplification of Siska Corporation as described in PCT Patent Publication WO 88/10315, or by the use of linear amplification. In this connection, the expression "linear amplification" is used herein to refer to amplification using a single primer for each diagnostic portion in the presence of an agent for polymerization and appropriate nucleotide triphosphates whereby amplification is effected by primer extension based on the use of a single strand of sample nucleic acid as template.

Where amplification is effected either by the use of diagnostic and amplification primers or by the use of two diagnostic primers, for example, as described in the first and second embodiments of the present invention or as part of the amplification procedure described in European Patent Publication No. 237,362, the steps of (a) denaturing to separate primer extension products from their template and (b) contacting single strands thereby obtained, either together or sequentially, with appropriate nucleoside triphosphates, an agent for polymerization of the nucleoside triphosphates, and the relevant primers to synthesize further extension produces; are preferably repeated at least five times (cycles) up to an indefinite number, especially where the sample DNA is refractory to amplification, without detriment to the present invention. More preferably 15–60, e.g., 15–30 times (cycles) are employed if the sample contains human genomic DNA. If the sample comprises cells, preferably they are heated to expose the nucleic acids therein to the reagents. This step avoids purification of the nucleic acids prior to reagent addition. In this regard, it will be appreciated that the present invention represents a substantial improvement over prior processes even if DNA purification from a sample is performed prior to the attempted amplification.

It will be appreciated that contact between the single strands produced by denaturation and the appropriate nucleoside triphosphates, an agent for polymerization of the nucleoside triphosphates, the primer(s), for example, the diagnostic primer(s) and/or the amplification primer(s) may be effected either by addition of these materials to the reaction mixture following separation of the primer extension product from its template (step a) or reliance may be placed on the materials already present in the reaction mixture. Indeed, any one or more different nucleoside triphosphates and/or the agent for polymerization and/or the primer(s), for example, the diagnostic primer(s) and/or the amplification primer may be added at any stage of the process of the invention.

Linear amplification may be effected by any convenient means and thus may be effected by the use of complementary nucleoside triphosphates in the presence of an agent for polymerization of the nucleoside triphosphates to produce primer extension products of indeterminate length where a sufficient degree of complementarity is present between the diagnostic primer and the sample nucleic acid. Preferably, where all complementary nucleoside triphosphates are to be employed, the sample nucleic acid is subjected to endonuclease digestion, the restriction endonuclease being selected so as to ensure that cleavage of the sample nucleic acid is effected at a site adequate to permit the formation of primer extension products of fixed length. Advantageously, however, the linear amplification may be effected in the presence of only 1, advantageously only 2 or preferably one 3 nucleoside triphosphates such that the diagnostic primer in its bound state (i.e., hybridized to the sample nucleic acid) can only extend as far as the presence of only the 1, 2 or 3 nucleoside triphosphates will permit. Once a nucleoside triphosphate is present in the sample nucleic acid for which no complementary nucleoside triphosphate is present, then primer extension will cease.

If desired, the linear amplification may be effected at the melting temperature (Tm) of the sequence. At this temperature, the diagnostic primer hybridized to the complementary sequence in the sample nucleic acid is in equilibrium with the diagnostic primer free in solution and thus the diagnostic primer (optionally in extended form) is being rapidly hybridized to and denatured from the sample nucleic acid. If desired, the linear amplification may also be effected by thermal oscillation. Such thermal oscillation would generally involve rapid temperature fluctuation about the melting temperature of the sequence.

The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose. In general, deoxyribonucleosides will be employed in combination with a DNA polymerase. It will be appreciated, however, that other modified bases capable of base pairing with one of the conventional bases adenine, cytosine, guanine, thymine and uracil may be employed. Such modified bases include, for example, 8-azaguanine and hypoxanthine.

The term "nucleotide" as used herein can refer to nucleotides present in either DNA or RNA and thus includes nucleotides which incorporate adenine, cytosine, guanine, thymine and uracil as base, the sugar moiety being deoxyribose or ribose. It will be appreciated, however, that other modified bases capable of base pairing with one of the conventional bases, adenine, cytosine, guanine, thymine and uracil, may be used in the diagnostic primer and amplification primer employed in the present invention. Such modified bases include, for example, 8-azaguanine and hypoxanthine.

The agent for polymerization from the nucleoside triphosphates may be any compound or system which will function to accomplish the synthesis of primer extension products, including enzymes. Suitable enzymes for this purpose include, for example, E. coli DNA Polymerase I, Klenow fragment of E. coli DNA polymerase I, T4 DNA polymerase, other available DNA polymerases, reverse transcriptase, and other enzymes, including thermostable enzymes. The term "thermostable enzyme" as used herein refers to any enzyme which is stable to heat and is heat resistant and catalyzes (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis terminates, producing molecules of different lengths. There may be enzymes for example, thermostable enzymes, however, which initiate synthesis at the 5' end and proceed in the other direction, using the same process as described above. A preferred thermostable enzyme which may be employed in the process of the present invention is that which can be extracted and purified from *Thermus aquaticus*. Such enzyme has a molecular weight of about 86,000–90,000 daltons as described in European Patent Publication No. 237,362 (see also European Patent Publication No. 258,017). *Thermus aquaticus* strain YT1 is available without restriction from the American Type Culture Collection, 12301 Parklawn Drive, Rockville, Md., USA as ATCC 25,104.

The term "complementary to" is used herein in relation to nucleotides to mean a nucleotide which will base pair with another specific nucleotide. Thus, adenosine triphosphate is complementary to uridine triphosphate or thymidine triphosphate and guanosine triphosphate is complementary to cytidine triphosphate. It is appreciated that whilst thymidine triphosphate and guanosine triphosphate may base pair under certain circumstances, they are not regarded as complementary for the purpose of this specification. It will also be appreciated that whilst cytosine triphosphates and adenosine triphosphate may base pair under certain circumstances, they are not regarded as complementary for the purposes of this specification. The same applies to cytosine triphosphate and uracil triphosphate.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. Thus, primer sequences (including the probe or priming regions in the diagnostic primer) do not necessarily have to be exactly complementary to the target sequences. Generally a small number of mismatches will be tolerated in the middle of the primer sequences and will allow hybridization and priming of extension products. In general, the degree of mismatching tolerated depends upon the primer length which in turn affects the denaturation temperature and the annealing temperature selected for practice of the PCR cycles. If the denaturation temperature of the primer is close to or higher than the annealing temperature (less stringent), then the primer will still prime to the target sequence despite a small number of (generally one or two or at most three) mismatches. The probe region may be capable of tolerating more mismatches in the middle of the sequence but it still depends on the denaturation temperature of the probe region and the annealing temperature of the selected PCR hybridization and extension conditions. Nevertheless, it is preferred that the priming and probe sequences be exactly complementary to their respective targets.

The term "amplification primer" is used herein to refer to a primer which is capable of hybridizing to the nucleic acid strand which is complementary to the nucleic acid strand to which the diagnostic primer is capable of hybridizing, the "amplification primer" having a nucleotide sequence such that it is capable of hybridizing to a diagnostic primer extension product, after separation from its complement, whereby the diagnostic primer extension product serves as a template for synthesis of an extension product of the amplification primer, thereby facilitating amplification. It should further be recognized that a second diagnostic primer of the invention which is specific for a second target sequence and second reference sequence may also be used as the amplification primer such that the nucleotide sequence of the amplification primer comprises (1) a priming region at its 3'-end which is substantially complementary to a target nucleic acid sequence on the complement of said sample nucleic acid, and (2) a probe region located 5' to said priming region which is substantially complementary to a second reference nucleic acid sequence which is noncontiguous with and 3' to the second target nucleic acid sequence on the complement of said sample nucleic acid strand.

A much simpler and preferred method of distinguishing between amplification products comprises selecting the nucleotide sequences of the amplification primers such that the length of each amplified product formed during the process of the present invention is different. In this regard the number of base pairs present in an amplification product is dictated by the distance between the target sequences of the diagnostic and amplification primers. Thus, the amplification primers may be designed such that each potential variant nucleotide is associated with a potential amplification product of different length.

The presence or absence of a given potential variant nucleotide may thus advantageously be detected by electrophoretic techniques, in which the different amplified products obtained may be distributed according to their molecular weight and thereby identified for example by autoradiography or fluorescent techniques.

Other aspects and advantages of the present invention will be understood upon consideration of the following illustrative examples.

EXAMPLE 1

According to this example, a single diagnostic primer according to the invention comprising a priming region and a probe region was used to distinguish the following HLA alleles (DRB1*03021, *03022, *0303 (serologically defined as DR18)) from the rest of the DRB1*03 alleles which are generally defined serologically as DR17. The target DNA was isolated from EBV-transformed human B-cell line using QIAmp Blood Kit (Qiagen, Inc. Santa Clara, Calif.).

As a control, primer OLR-14(5'-CTTGGAGTACTCT ACGTCT-3'; 10 pmole) (SEQ ID NO: 1) co-responding to amino acid 8–13 of DRB1 and primer OLR-142(5'-GCAGTAGTTGTCCACCCG-3'; 10 pmole) (SEQ ID NO: 2) corresponding to amino acid 74–79 were used as PCR primers according to conventional practice wherein all PCR reactions are performed using a Perkin-Elmer Gene-Amp PCR System 9600 the following conditions: 10 mM Tris (hydroxymethyl)aminomethane Hydrochloride (pH 8.3 @ 25(C); 50 nM Potassium Chloride, 14.5 mM Magnesium Chloride, 0.001% (w/v) Gelatin, 200(M dNTP's (dATP, dCTP, dGTP, dTTP), 6% (w/v) Sucrose, 0.002% (w/v) Cresol Red at 10 microliters total reaction volume with the PCR Reaction profile set out below:

| No. of Cycles | Step | Temp (° C.) | Time (sec.) |
|---|---|---|---|
| 1 | 1 | 96 | 130 |
|  | 2 | 63 | 60 |
| 9 | 1 | 96 | 10 |
|  | 2 | 63 | 60 |
| 20 | 1 | 96 | 10 |
|  | 2 | 59 | 50 |
|  | 3 | 72 | 30 |

Primers OLR-147 and OLR-148 which amplify a 750 base-pair fragment of the Human beta-Globin gene were included in all PCR to serve as the internal control for proper PCR amplification.

According to the control experiment, the following 13 (thirteen) DRB1* alleles were amplified: DRB1*03011, DRB1*03012, DRB1*03021, DRB1*03022, DRB1*0303, DRB1*0304, DRB1*0305, DRB1*0306, DRB1*0307, DRB1*0308, DRB1*0309, DRB1*03010, and DRB1*1107.

The experiment was then repeated with a primer according to the invention containing a priming region and a probe region separated by a spacer. Note: An extra "A" was inserted between the probe and primer regions to separate these two sequences, because the nucleotide at the 5'-end of the primer region, a "G", is the same as the next nucleotide 3'-end to the probe region. Without insertion of the "A" spacer, the probe region extends one more nucleotide thus increasing the melting temperature of the probe region by approximately 4° C. Specifically, when diagnostic primer OLR-1414 (5'-TTGGAGTACTCTACGTCTGAAGG TTCCTGGAG-3'; 10 pmole) (SEQ ID NO: 3) co-responding to amino acids 8–14 (with underlined sequence) and 25–28 (with bolded sequence) of DRB1 with a gap of 32 base pairs and conventional amplification primer OLR-142(5'-GCAGTAGTTGTCCACCCG-3'; 10 pmole) (SEQ ID NO:2) co-responding to amino acid 74–79 were used, only the following three alleles were amplified: DRB1*03021, DRB1*03022, and DRB1*0303. Accordingly, use of the Primer OLR-1414 provides a substantial improvement over the use of conventional primers.

EXAMPLE 2

According to this example, the method of the invention is practiced in a manner which demonstrates that because the primer region of the diagnostic primers of the invention can direct the PCR reaction under the sub-optimal condition, that a mismatch in the primers is not required to be at the 3'-end of the primer to perform successful PCR-SSP. Specifically, the primers OLR-1419 (5'-TTGGAGTACTCTACGTCTGATICCTGGAGAGA-3'; 10 pmole) (SEQ ID NO: 4) and OLR-1420(5'-TTGGAGTACTCTACGTCTGATCCTGGAGAGATA-3'; 10 pmole) (SEQ ID NO:5) which have the same probe region(the underlined sequence) but have slightly different primer regions to OLR-1414 (5'-TTGGAGTACTCTACGTCTGAA-GGTICCTGGAG-3'; 10 pmole) (SEQ ID NO: 3) were used to amplify target DNA according to the method of Example 1. The differences between DRB1*0301 and DRB1*03021, *03022, *0303 are indicated by bold and underlined residues. When these three primers are individually paired with OLR-142 as an amplification primer, all primer pairs successfully amplify the DRB1*03021 allele but not the DRB1*0301 allele. This example demonstrates that even with the mismatch between DRB1*0301 and DRB1*03021, *03022, *0303 6 nucleotides away from the 3'-end, the primer of the invention can still be used to selectively amplify the desired allele.

EXAMPLE 3

According to this example two primers comprising priming regions and probe regions separated by a spacer region were used to amplify target sequences according to the methods of the invention. Specifically, OLR-1334 (5'-GACCGGAACACACGGTTGGCCCAGT-3') (SEQ ID NO: 6) which recognizes the amino acid sequence of 61–65 and 69–71 of the HLA-A (mature protein sequence) and OLR-1348(5'-ACTCACCGTCCTCGCAATAGTAGCC-3') (SEQ ID NO: 7) which recognizes the amino acid sequence of 91–88(plus 6 nucleotides of the intron 3) and 85–83 of the HLA-A were used to perform PCR. The underlined sequence in these two primers represents the probe region and the bolded sequence represents the primer region. A "TT" sequence was inserted between the probe and primer region as a spacer. This primer pair amplifies only the following alleles: A*3401, A*3402, and A*6601.

However, if only the probe region of each primer were used as the PCR-SSP primers, the following extra alleles will be amplified: A-2501, A-2502 A-2601, A-2602, A-2603, A-2604, A-2605, A-2606, A-2608, A-2609, A-2610, and A-2611N. Accordingly, the primers of the present invention can be effectively used as pairs of primers in polymerase chain reaction to increase the specificity of PCR-SSP.

Numerous modifications and variations in the practice of the invention are expected to occur to those skilled in the art upon consideration of the presently preferred embodiments thereof.

What is claimed is:

1. A method for detecting the presence of a target nucleic acid sequence on a sample nucleic acid strand from an individual comprising the steps of: treating the sample, together or sequentially with appropriate nucleoside triphosphates, an agent for polymerization of the nucleoside triphosphates, a diagnostic primer and an amplification primer under hybridizing conditions;

wherein the nucleotide sequence of said diagnostic primer comprises (1) a priming region at its 3'-end which is substantially complementary to the target nucleic acid sequence, and (2) a probe region located 5' to said priming region which is substantially complementary to a reference nucleic acid sequence which is 3' to the target nucleic acid sequence on the sample nucleic acid strand wherein when said reference nucleic acid sequence is contiguous with said target nucleic acid sequence on the sample nucleic acid strand then the priming region and probe region on the diagnostic primer are separated by a spacer region of nucleic acid, and further wherein when the priming region and the probe region on the diagnostic primer are contiguous then there exists an intervening sequence between the reference nucleic acid sequence and the target nucleic acid sequence on the sample nucleic acid strand;

whereby for selected hybridization and extension conditions the lengths of the priming region and the probe region are such that an extension product of the diagnostic primer is synthesized when both the priming region is substantially complementary to the target nucleic acid sequence and the probe region is substantially complementary to the reference nucleic acid sequence, but wherein for said selected hybridization and extension conditions no extension product of the diagnostic primer is synthesized when either the priming region or the probe region are not substantially complementary to the target and reference nucleic acid sequences respectively;

any extension product of the diagnostic primer formed being capable of serving as a template for synthesis of an extension product of said amplification primer after separation from its complement;

amplifying any extension product to produce an amplification product; and detecting the presence or absence of the target polynucleic acid sequence from the presence or absence of amplification product obtained as above.

2. The method of claim 1 wherein said priming region and said probe region on the diagnostic primer are separated by a spacer region of nucleic acid sequence which is not complementary to the sequence of the sample nucleic acid strand between the target and reference sequences.

3. The method of claim 2 wherein said spacer is from 1 to 30 bases long.

4. The method of claim 2 wherein said spacer is from 8 to 30 bases long.

5. The method of claim 1 wherein said target nucleic acid sequence is from 1 to 350 bases from said reference nucleic acid sequence on a sample nucleic acid sequence.

6. The method of claim 1 wherein the priming region and probe regions are exactly complementary to the target and reference nucleic acid sequences respectively.

7. The method of claim 1 wherein the target nucleic acid sequence is characteristic of a human leukocyte antigen (HLA).

8. The method of claim 1 wherein the nucleotide sequence of said amplification primer comprises (1) a priming region at its 3'-end which is substantially complementary to a second target nucleic acid sequence on the complement of said sample nucleic acid, and (2) a probe region located 5' to said priming region which is substantially complementary to a second reference nucleic acid sequence which is 3' to the second target nucleic acid sequence on the complement of said sample nucleic acid strand wherein when said second reference nucleic acid sequence is contiguous with said second target nucleic acid sequence on the sample nucleic acid strand then the priming region and probe region on the amplification primer are separated by a spacer region of nucleic acid.

\* \* \* \* \*